United States Patent [19]

Rice et al.

[11] 4,413,911
[45] Nov. 8, 1983

[54] GAS ANALYZER WITH FLUID CURTAIN

[75] Inventors: Richard G. Rice, Cupertino; Mathew G. Boissevain, Los Altos Hills; Robert R. Dubin, San Jose, all of Calif.

[73] Assignee: Measurex Corporation, Cupertino, Calif.

[21] Appl. No.: 257,063

[22] Filed: Apr. 24, 1981

[51] Int. Cl.³ ............................................... G02B 7/00
[52] U.S. Cl. ..................................... 356/438; 350/584
[58] Field of Search ............... 356/436, 437, 438, 439, 356/442; 250/573, 576; 350/584

[56] References Cited

U.S. PATENT DOCUMENTS

| | | | |
|---|---|---|---|
| 3,628,028 | 12/1971 | Thorsheim | 250/576 |
| 3,833,305 | 9/1974 | Porter et al. | 356/438 |
| 3,838,925 | 10/1974 | Marks | 250/573 |
| 3,895,233 | 7/1975 | Boll et al. | 356/437 |
| 4,126,396 | 11/1978 | Hartmann et al. | 356/438 |
| 4,205,550 | 6/1980 | Swanson | 356/438 |
| 4,225,243 | 9/1980 | Typpo | 356/439 |
| 4,277,131 | 7/1981 | Hart et al. | 356/439 |

Primary Examiner—R. A. Rosenberger
Attorney, Agent, or Firm—Hal J. Bohner

[57] ABSTRACT

A gas analyzer capable of measuring select properties of gas includes a source for emitting a beam of radiation and a detector for receiving the radiation, with the beam aligned to impinge the detector. A housing for enclosing the beam has two apertures permitting the gas to enter the housing through one of the apertures to intercept the beam, and to exit from the housing through the other aperture. Nozzles capable of generating fluid curtains are positioned to intercept the beam and are positioned to define a zone in the housing within which zone the gas is confined.

8 Claims, 11 Drawing Figures

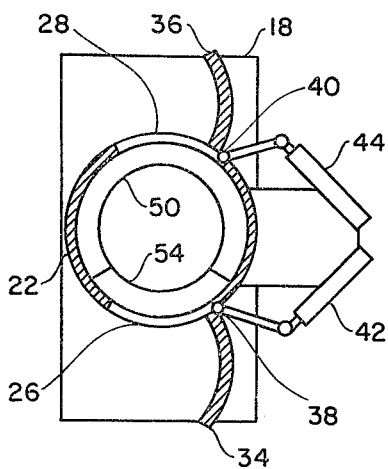
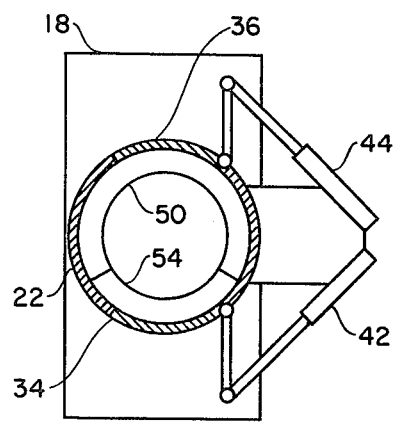
FIG. 2                    FIG. 3
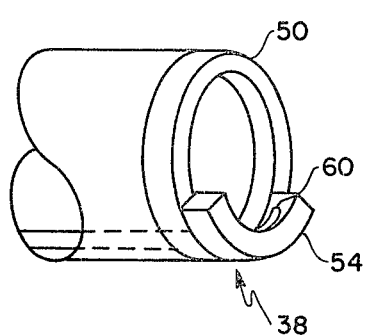
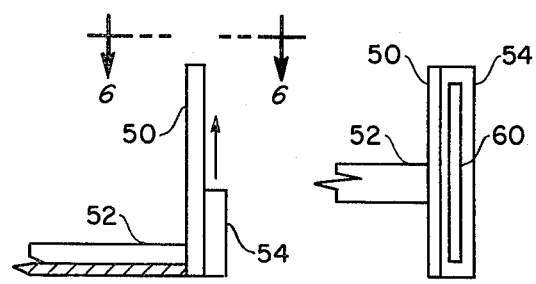
FIG. 4         FIG. 5         FIG. 6

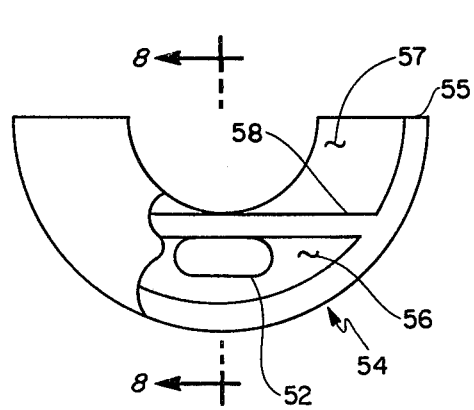
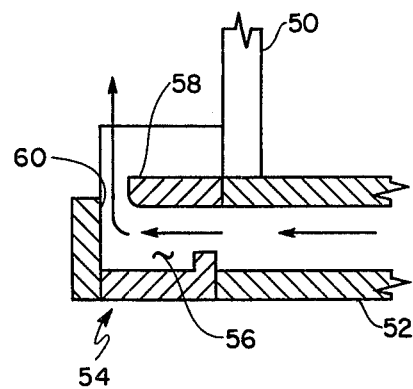
FIG. 7        FIG. 8
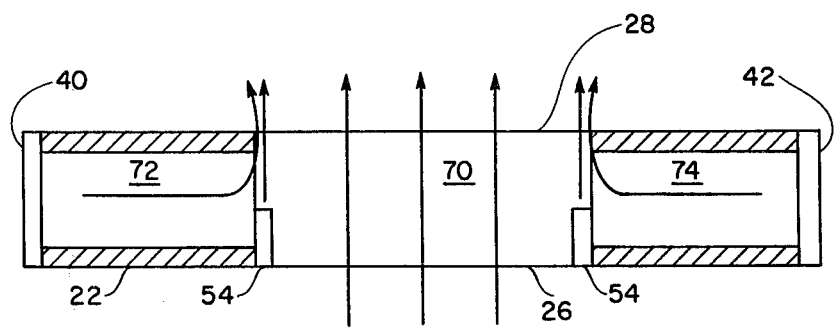
FIG. 9

GAS ANALYZER WITH FLUID CURTAIN

BACKGROUND OF THE INVENTION

The Field of The Invention

The present invention relates to an apparatus for analyzing a gas. In particular, the present invention relates to a gas analyzer with a fluid curtain to define a region to contain the gas to be measured. Typically, the gas being analyzed is exhaust gas produced as a result of combustion of liquid or solid fuel.

State of The Art

Gas analyzers for monitoring the products of combustion in a stack are taught, for example, in U.S. Pat. Nos. 4,225,243 and 3,895,233. In U.S. Pat. No. 3,895,233 the gas analyzer includes a housing having two apertures, one permitting the gas to enter into the housing where it can be analyzed, and the other aperture permitting the gas to exit from the housing.

In the analyzer taught in the patent, the gas is analyzed by transmitting a beam of radiation through the gas and measuring the attenuation of the beam. It can be seen that the length of the gas-filled zone through which the beam travels affects the degree of attenuation and thus the measured concentration of the gas. It has been found, however, that in gas analyzers of the type taught in the patent, once the gas enters the housing, the gas may diffuse or become turbulent causing instability in the length of the gas-filled zone. That is, the length of the gas-filled zone may vary with time and with varying conditions of the gas. The instability in the length of the zone causes inaccuracy and lack of repeatability of the gas analysis.

Objects of The Invention

It is an object of the present invention to provide a gas analyzer having a source, capable of emitting a beam of radiation, a detector, with the beam aligned to impinge the detector and means to maintain the gas-filled zone a predetermined length. It is a further object of the invention to provide an analyzer having nozzle means, capable of generating a fluid curtain, to define a region in said housing means, within which said region the gas to be analyzed is confined.

Further objects and advantages of the present invention can be ascertained with reference to the specification and drawings herein, which are offered by way of example and not in limitation of the invention which is defined by the claims and equivalents thereto.

BRIEF DESCRIPTION OF THE DRAWINGS

FIG. 2 is a section view of FIG. 1 taken along line 2—2.

FIG. 3 is the same sectional view as FIG. 2 with the apparatus in a different operating mode.

FIG. 4 is a perspective view of a portion of the gas analyzing apparatus, showing the nozzle means in the apparatus.

FIG. 5 is a side view of the nozzle means.

FIG. 6 is a top view of the nozzle means.

FIG. 7 is a detailed view of part of the device shown in FIGS. 4–6.

FIG. 8 is a cross-sectional view of the device shown in FIG. 7, taken along line 8—8.

FIG. 9 is a schematic side view showing the direction and manner of gas flow in the operation of the apparatus.

DETAILED DESCRIPTION OF THE PREFERRED EMBODIMENT

Figure 1:
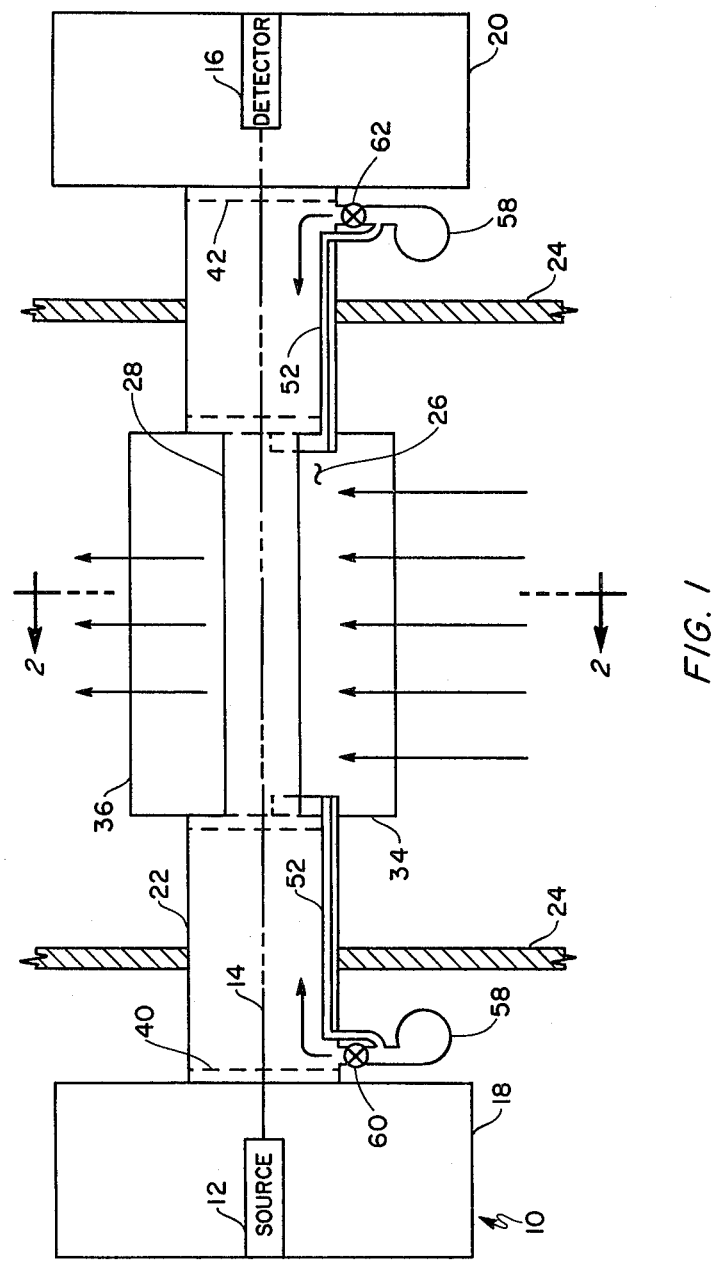
FIG. 1 is a side view of the gas analyzing apparatus of the present invention.
Figure 10:
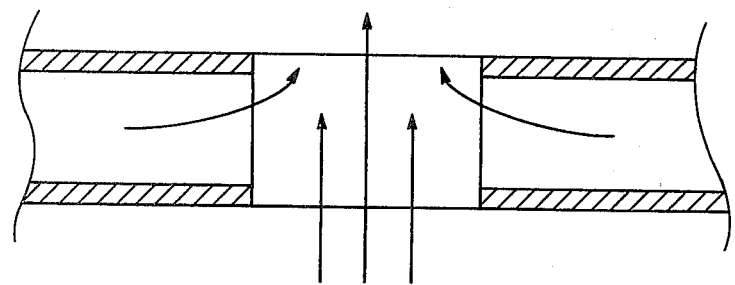
FIG. 10 is a schematic side view of the direction and manner of gas flow in a gas analyzing apparatus of the prior art.
Figure 11:
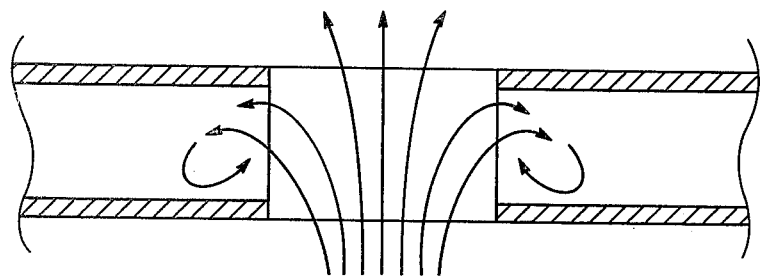
FIG. 11 is another schematic side view of the direction and manner of gas flow in a gas analyzing apparatus of the prior art.

Referring to FIG. 1, there is shown a gas analyzing apparatus 10 according to the preferred embodiment of the present invention. The apparatus 10 comprises a source 12, capable of emitting a beam 14 of radiation. The beam 14 is aligned to impinge a detector 16. The source 12 is contained in a first enclosure 18. The first enclosure 18 provides a suitable environment such as an atmosphere with regulated temperature and humidity for the source 12 and its associated electronics. Similarly, the detector 16 is in a second enclosure 20. The second enclosure 20 provides suitable environmental conditions for the operation of the detector 16 and its associated electronics.

A cylindrical housing 22 encloses the beam 14. The housing 22 is typically placed across a stack 24, which is the exhaust output of a furnace to carry the gaseous by-products of combustion from the furnace. The housing 22 has two apertures 26 and 28 permitting the stream of gas flowing through the stack 24 to enter the housing 22, to intercept the beam 14, and to exit from the housing 22. The gas of the stack 24 flowing in the direction as shown by the arrows, enters the housing 22 through the first aperture 26, intercepts the beam 14 and exits from the second aperture 28. A first door 34 is adapted to close the first aperture 26. Similarly, a second door 36 is adapted to close the second aperture 28. Two glass windows 40 and 42 are sealingly coupled respectively to the left and right ends of the housing 22 to prevent gases from flowing from the housing 22 into the enclosures 18 or 20.

Turning to FIGS. 2 and 3, the doors 34 and 36 are illustrated in greater detail. The doors 34 and 36 are coupled to the housing 22 by hinges 38 and 40, respectively. Two hydraulic cylinders 42 and 44 are coupled to the housing 22 adjacent the doors 34 and 36. The hydraulic cylinders can be operated to open the doors as shown in FIG. 2 and to close the doors as shown in FIG. 3. This door system is discussed in U.S. patent application Ser. No. 919,442 filed June 6, 1978 now abandoned, which is incorporated by reference herein.

Turning again to FIG. 1, nozzle means 38 and 39 are positioned to define a region in the housing 22 within which the stack gas is substantially confined. In particular, the nozzle means 38 and 39 are capable of generating a fluid curtain which intercepts the beam 14 at a direction substantially perpendicular to the beam 14. The fluid curtain generated by the nozzle means 38 and 39 is moving substantially parallel to the direction of flow of the gas flowing through the stack 24 as shown by the arrows. Each of said nozzle means 38 and 39 is placed at the extremities of the first aperture 26 and is capable of generating a fluid curtain directed to impinge the ends of the second aperture 28.

Details of the nozzle means 38 are shown in FIGS. 4–8, it being understood that nozzle means 39 is substantially the same. The nozzle means 38 includes a ring 50, a conduit 52, and a plenum chamber 54.

The ring 50 is coupled to the housing means 22, and the plenum chamber 54 is coupled to the ring 50 outside the housing 22. The plenum chamber 54 includes a casing 55 shaped in the form of an annular section having indentations in one face thereof. In particular, the casing has a lower indentation 56 formed in communication with the conduit 52 and an upper indentation 57 spaced apart from the lower indentation 56 so that a horizontal rib 58 is formed therebetween. A plate 59 is affixed to the casing 55 to cover the lower indentation 56 and the rib 58. Thus the chamber is formed to receive air from the conduit 52. The rib 58 is spaced apart from the plate 59 to form a slot 60 therebetween. In practice the slot is about 0.010 to 0.060 inch wide and preferably about 0.030 inch wide.

The conduit 52 is coupled at one end in fluid-flow communication with the plenum chamber 54 while the opposite end of the conduit 52 is coupled to a source of pressurized fluid, blower 62. Thus a stream pressurized fluid, which in practice is air, can be introduced into the plenum 54 to flow from the orifice 56 to provide a fluid curtain substantially parallel to the stream of gas flowing through the stack 24. The plenum chamber 54 and the nozzle orifice 56 are positioned adjacent to the edge of aperture 26. The fluid barrier generated by the nozzle means 38 is directed towards the second aperture 28, in a direction substantially perpendicular to the beam 14 and substantially parallel to the flow of the gas 28 through the stack 24.

With further reference to FIG. 1, the conduits 52 are shown coupled to blowers 62. Blowers 62 are also coupled to introduce a stream of pressurized air into each end of housing 22 near the windows 40 and 42. Valves 64 and 66 are provided to permit control of the streams of air from the blowers 62 into the housing 22.

Referring to FIG. 7 there is shown a schematic side view of the direction and manner of gas flow in the operation of the apparatus of the present invention. Gas from the stack 24 enters the housing 22 via the first aperture 26 in the direction shown by the arrows. The gas then exits from the housing 22 via the second aperture 28. The fluid curtains generated by the nozzle means 38 and 39 are shown as arrows. In practice the velocity of air forming the air curtain is preferably about 40-60 miles per hour. The air streams generated by the blowers 62 flow through the housing 22 as shown by the arrows. As can be seen the fluid curtains generated by the nozzle means 38 and 39 substantially confine the gas from the stack 24 to a zone 70 between the fluid curtains. Similarly, the fluid curtains confine the air stream from the blowers 62 to a zone 72 extending from the left window 40 to the zone 70 and to another zone 74 extending from the right window 42 to the zone 70. It should be understood that the fluid curtains are not completely impermeable barriers, and in some cases there may be some deviation from the ideal situation illustrated in FIG. 7.

It has been found that it is important to control the flow of air from slots 60, relative to the flow of air through the housing 22. The utilization of valves not shown permits such control. In practice, means other than valves can be used to vary the flow of air. For example, discs having orifices of different sizes can be inserted in the conduits connecting the blowers to the housing 22.

We have found that it is important to calibrate an air curtain system when it is actually installed. The calibration procedure includes measuring the concentration of a gas in the stack, for example carbon dioxide, $CO_2$, with a conventional, wet chemical method. Then the present system is used to take a series of measurements of the concentration of $CO_2$ while varying the ratio of air through the conduits 52 relative to the air directly into the housing 22. We normally find that there is a range of ratios which result in good agreement between the concentration of $CO_2$ measured by the present system and the concentration measured by the conventional, wet chemical method. Normally, the ratio of air flow in the air curtain relative to the flow of air through the housing 22 is maintained in the ratio of between one-to-one and four-to-one, in term of the volumetric rates of flow.

The operation of the apparatus 10 of the present invention is in marked contrast to that of the prior art shown in FIGS. 8 and 9. Without the fluid curtain generated by the nozzle means 38 and 39, gas from the blowers 62 may commingle with the gas from the stack 24, as shown by FIG. 8, resulting in a dilution of the stack gas, thereby giving a false reading of select properties of the stack gas. Alternatively, without the fluid curtain, gas from the stack 24 may enter the housing means 22 and diffuse in the housing means 22, as shown in FIG. 9, again giving a false reading. This may be especially true at high rates of flow of the stack gas.

The theoretical basis for the present invention may be understood as follows. The measurement of the select properties of gas is made in accordance with Beer's Law, i.e., $I = I_0 e^{-ucL}$ where $I$ = Intensity of measured radiation with the gas, $I_o$ = Intensity of measured radiation without the gas, $u$ = absorption coefficient, $C$ = concentration of gas, $L$ = path length of the gas.

In the apparatus of the present invention, the gas to be analyzed is confined to a well defined region. This is in essence controlling the variable $L$, the path length of the gas, to a constant value. By confining the gas to a well defined region, the accuracy and repeatability of the variable $L$ is assured, thereby assuring the accuracy and repeatability of the measurement of the select properties of the gas.

The embodiment illustrated and described herein includes a detector 16 located on the opposite side of the stack from the source 12. Alternatively, the source and detector can be located on the same side of the stack and a reflector located on the opposite side. Thus the beam of radiation travels from the source, through the stack and is reflected back through the stack to impinge the detector.

We claim:

1. Apparatus for analyzing a first gas stream comprising:
   (a) a source capable of emitting a beam of radiation;
   (b) a detector located so that the beam passes through the first gas stream and impinges the detector;
   (c) housing means enclosing at least part of the beam;
   (d) means for filling the housing means with a second gas; and
   (e) nozzle means coupled to said housing means for providing a curtain of fluid substantially between the second gas in said housing means and the first gas stream to substantially prevent the first gas stream from mixing with the second gas inside said housing means.

2. An apparatus according to claim 1 wherein said nozzle means is constructed and arranged to provide a curtain of fluid between about 0.010 and 0.060 inch in thickness.

3. An apparatus according to claim 1 wherein said nozzle means is constructed and arranged so that the curtain of fluid travels in a direction substantially perpendicular to the beam of radiation.

4. An apparatus according to claim 1 wherein said nozzle means includes means located in the first gas for discharging fluid.

5. Apparatus according to claim 1 wherein said nozzle means is constructed and arranged to direct the fluid curtain into the first gas to mix therewith.

6. Apparatus for analyzing a first gas stream comprising:
   (a) a source capable of emitting a beam of radiation;
   (b) a detector located so that the beam passes through the first gas stream and impinges said detector;
   (c) source housing means for enclosing part of the beam adjacent said source;
   (d) detector housing means for enclosing part of the beam adjacent said detector; and
   (e) nozzle means coupled to said source housing means and to said detector housing means for providing curtains of fluid to substantially prevent the first gas from entering said source housing means and said detector housing means wherein said nozzle means includes two nozzles spaced apart from one another to define a first zone inside said source housing means, a second zone inside said detector housing means and a third zone between said first and second zones, wherein said nozzles are located one between the first and third zones and one between second and third zones.

7. An apparatus according to claim 6 further including means for filling said source housing means and said detector housing means with a second gas.

8. An apparatus according to claim 6 wherein said nozzle means is constructed and arranged so that said fluid curtains are directed in a direction substantially parallel to the flow of gas in the first gas stream.

* * * * *